(12) United States Patent
Pandey et al.

(10) Patent No.: US 10,357,274 B2
(45) Date of Patent: Jul. 23, 2019

(54) SURGICAL TOOL FOR CORING PRECISE HOLES AND PROVIDING FOR RETRIEVAL OF TISSUE

(75) Inventors: Rajesh Pandey, Plantation, FL (US); Charles R. Shambaugh, Jr., Coral Gables, FL (US)

(73) Assignee: HeartWare, Inc., Miami Lakes, FL (US)

( * ) Notice: Subject to any disclaimer, the term of this patent is extended or adjusted under 35 U.S.C. 154(b) by 586 days.

(21) Appl. No.: 12/087,715

(22) PCT Filed: Jan. 12, 2007

(86) PCT No.: PCT/US2007/000764
§ 371 (c)(1),
(2), (4) Date: Aug. 25, 2008

(87) PCT Pub. No.: WO2007/084340
PCT Pub. Date: Jul. 26, 2007

(65) Prior Publication Data
US 2009/0012552 A1    Jan. 8, 2009

Related U.S. Application Data

(63) Continuation-in-part of application No. 11/332,016, filed on Jan. 13, 2006.

(51) Int. Cl.
*A61B 17/3205* (2006.01)
*A61B 17/11* (2006.01)
*A61B 17/00* (2006.01)

(52) U.S. Cl.
CPC ........ *A61B 17/32053* (2013.01); *A61B 17/11* (2013.01); *A61B 2017/00252* (2013.01); *A61B 2017/1107* (2013.01)

(58) Field of Classification Search
CPC .............. A61B 17/11; A61B 17/32053; A61B 17/3205; A61B 2017/1107;
(Continued)

(56) References Cited

U.S. PATENT DOCUMENTS 3,776,237 A    12/1973 Hill et al.
4,018,228 A *   4/1977 Goosen ......................... 606/184
(Continued)

FOREIGN PATENT DOCUMENTS

| EP | 0637435 A1 | 2/1995 |
|---|---|---|
| WO | WO 02/45602 A | 6/2002 |
| WO | WO 2007/084340 | 7/2007 |

OTHER PUBLICATIONS

International Preliminary Report on Patentability issued by the International Bureau of WIPO in connection with International Application No. PCT/US2007/000764.
(Continued)

*Primary Examiner* — Sarah A Simpson
(74) *Attorney, Agent, or Firm* — Christopher & Weisberg, P.A.

(57) ABSTRACT

A tool for coring a hole in a portion of a patient's body. A cylindrical sheath includes a hollow bore open at both ends. A shaft is axially movable back and forth within the bore. A blade assembly is attached to one end of the shaft. The blade assembly comprises a hollow open cup portion having a closed end and a cutting edge formed around the margin of the open end. An interface is attached to the sheath which is shaped and dimensioned to communicate with a connector used to connect a medical device to a patient's body.

22 Claims, 6 Drawing Sheets

(58) Field of Classification Search
CPC ........... A61B 2017/00252; A61B 2017/00247; A61B 17/32075
USPC ................................. 606/184, 185, 167, 170
See application file for complete search history.

(56) References Cited

U.S. PATENT DOCUMENTS

| | | | |
|---|---|---|---|
| 4,461,305 | A | 7/1984 | Cibley |
| 5,129,913 | A | 7/1992 | Ruppert |
| 5,139,508 | A * | 8/1992 | Kantrowitz ...... A61B 17/32053 606/172 |
| 5,324,300 | A | 6/1994 | Elias et al. |
| 5,488,958 | A | 2/1996 | Topel et al. |
| 5,653,705 | A * | 8/1997 | de la Torre ........ A61B 17/3423 606/1 |
| 5,690,662 | A | 11/1997 | Chiu et al. |
| 5,695,504 | A * | 12/1997 | Gifford et al. ................. 606/153 |
| 5,827,316 | A * | 10/1998 | Young et al. .................. 606/185 |
| 5,965,504 | A | 10/1999 | Reynolds |
| 5,972,014 | A * | 10/1999 | Nevins ............. A61B 17/32053 604/165.02 |
| 5,980,545 | A | 11/1999 | Pacala et al. |
| 6,033,419 | A | 3/2000 | Hamblin, Jr. et al. |
| 6,036,657 | A | 3/2000 | Milliman et al. |
| 6,080,173 | A * | 6/2000 | Williamson et al. ......... 606/184 |
| 6,080,176 | A * | 6/2000 | Young ........................... 606/185 |
| 6,117,130 | A | 9/2000 | Kung |
| 6,162,124 | A | 12/2000 | Mueller et al. |
| 6,162,214 | A | 12/2000 | Mueller et al. |
| 6,171,251 | B1 | 1/2001 | Mueller et al. |
| 6,652,552 | B2 | 11/2003 | DuMontelle |
| 6,695,859 | B1 | 2/2004 | Golden et al. |
| 6,726,648 | B2 * | 4/2004 | Kaplon et al. .................... 604/9 |
| 6,732,501 | B2 | 5/2004 | Yu et al. |
| 6,863,677 | B2 | 3/2005 | Breznock |
| 2001/0020139 | A1 | 9/2001 | Milliman et al. |
| 2002/0177865 | A1 * | 11/2002 | McIntosh ...................... 606/184 |
| 2003/0023255 | A1 | 1/2003 | Miles et al. |
| 2004/0049221 | A1 | 3/2004 | Loshakove et al. |
| 2004/0073247 | A1 * | 4/2004 | Loshakove et al. .......... 606/184 |
| 2004/0236170 | A1 | 11/2004 | Kim |
| 2005/0101983 | A1 | 5/2005 | Loshakove et al. |
| 2005/0154411 | A1 | 7/2005 | Breznock et al. |
| 2007/0066943 | A1 * | 3/2007 | Prasad ................. A61M 1/3653 604/264 |
| 2007/0134993 | A1 | 6/2007 | Tamez et al. |
| 2007/0167968 | A1 | 7/2007 | Pandey |
| 2007/0167969 | A1 | 7/2007 | Pandey |

OTHER PUBLICATIONS

Written Opinion of the International Searching Authority issued by the International Searching Authority (ISA/US) in connection with International Application No. PCT/US2007/000764.
Office Action dated Jul. 24, 2008 in connection with U.S. Appl. No. 11/332,016, filed Jan. 13, 2006.
Office Action dated Feb. 11, 2009 in connection with U.S. Appl. No. 11/332,016, filed Jan. 13, 2006.
Advisory Action dated Jun. 24, 2009 in connection with U.S. Appl. No. 11/332,016, filed Jan. 13, 2006.
Communication from the Search Division of the European Patent Office dated Nov. 27, 2009 in connection with European Patent Application No. 07709706.1.
Supplementary European Search Report issued by the Search Division of the European Patent Office dated Nov. 18, 2009 in connection with European Patent Application No. 07709706.1.
International Search Report issued by the International Searching Authority (ISA/US) in connection with International Application No. PCT/US07/00764.
Written Opinion of the International Searching Authority issued by the International Searching Authority (ISA/US) in connection with International Application No. PCT/US07/00764.

\* cited by examiner

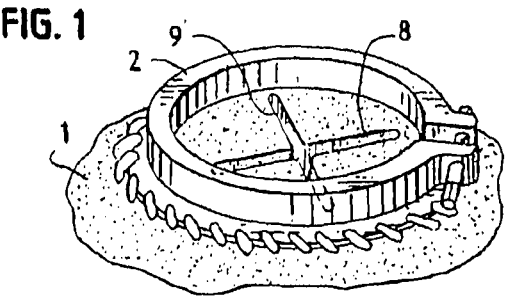
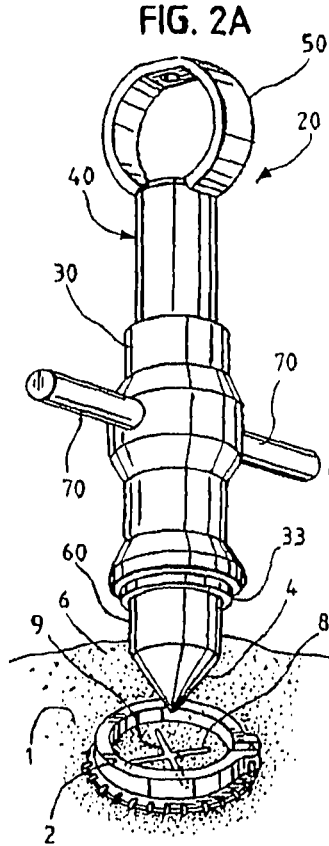
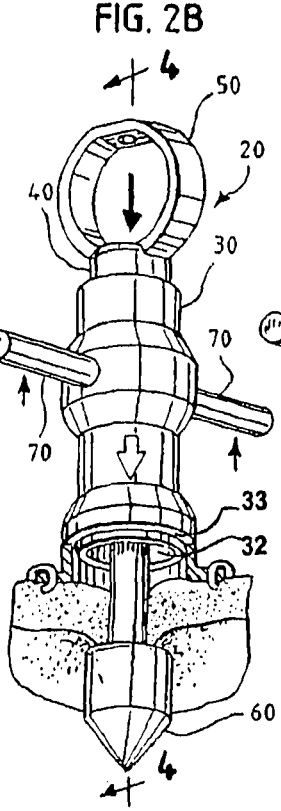
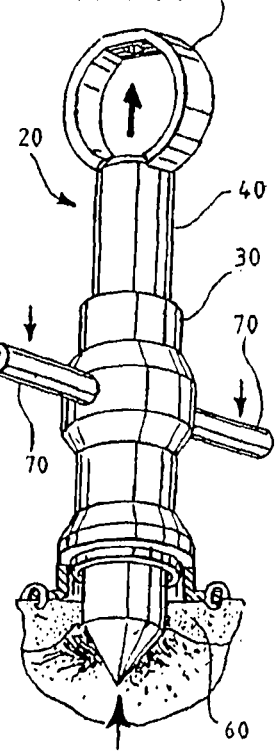

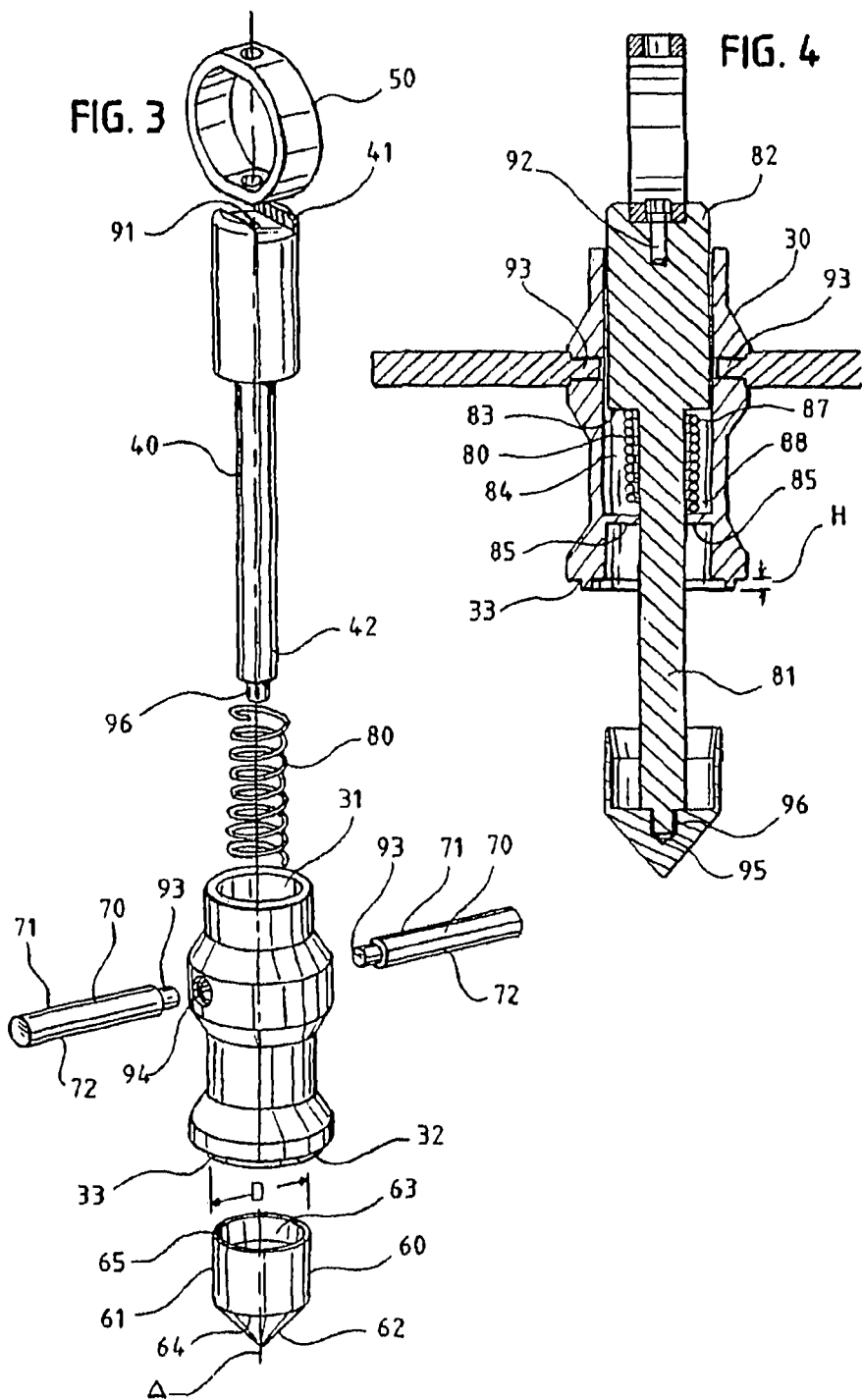

SURGICAL TOOL FOR CORING PRECISE HOLES AND PROVIDING FOR RETRIEVAL OF TISSUE

This application is a § 371 national stage of PCT International Application No. PCT/US2007/000764, filed Jan. 12, 2007, and claims the benefit of U.S. Ser. No. 11/332,016, filed Jan. 13, 2006, the contents of all of which are hereby incorporated by reference into this application.

BACKGROUND

A heart pump, such as a ventricular assist device ("VAD"), aids people suffering from severe ventricular heart failure in leading active and productive lives. A heart pump is typically connected to the left ventricle of the heart. One end of a tube, such as a graft, is connected to the heart pump and the other end is connected to the ascending aorta or the descending aorta. Once connected, the heart pump pumps blood from the left ventricle to the ascending or descending aorta to improve blood flow.

To connect a heart pump to a patient, surgeons use a connector, called a sewing ring. A sewing ring is attached to the myocardium of the heart by the use of sutures. A hole is then cored in the myocardium that acts as an entry site for a ventricular assist device. An inflow tube or cannula from the heart pump is inserted through this hole. For the implantation to be successful, however, the cored hole must be centered within the sewing ring and sized appropriately with respect to the sewing ring so that there is minimal leaking between the ventricular wall and the installed inflow tube.

To initiate coring, a surgeon must first make a manual "cross" or "crux" cut in the ventricle wall. A retractable coring tool is then inserted through the crux cut and used to form the hole. If the surgeon is not careful, the hole can be formed off-center with respect to the sewing ring, or the tissue that is cored from the heart can fall into the ventricle. Either of these situations can have negative effects on the transplant procedure. For instance, if the hole is not centered relative to the sewing ring, bleeding can occur at the inflow tube—ventricle interface. Moreover, the ease of placement of the VAD is degraded. If cored tissue falls into the ventricle, the surgeon will have to retrieve the tissue, thereby increasing blood loss due to additional time added to the procedure. Accordingly, what is needed is a coring tool that allows surgeons to core a precise hole in the center of the sewing ring and to easily retrieve the cored tissue so as to prevent the tissue from falling into the ventricle.

SUMMARY OF THE INVENTION

In one embodiment, a tool for coring a round hole in a patient's body is provided. The tool includes a housing having a longitudinal central bore defining a first opening at one end and a second opening at the other end. The central bore defines an axis along which a shaft within the bore is moved back and forth during operation of the tool. A blade assembly is attached to the lower end of the shaft. An interface structure is attached to or formed as part of the housing, which is shaped and dimensioned to communicate with a connector or sewing ring used to connect a medical device to a person's body.

In one embodiment, the shaft comprises an upper first end that protrudes from the first opening defined by the bore in the tool housing and a second lower end that protrudes from the second or lower opening defined by the bore in the tool housing. The first shaft end includes an actuating mechanism to allow a user to move the shaft within the housing. In one embodiment, the actuating mechanism comprises a ring which may be rotatably or fixedly attached to the first end of the shaft. The blade assembly is attached to the lower or second end of the shaft. With respect to a sewing ring, the tool interface comprises an annular ridge that extends from the housing and surrounds at least a portion of the second opening of the housing. The second opening of the housing and the ridge are circular and the ridge surrounds the second opening. When the ridge engages the upper surface of the sewing ring the blade assembly is centered with respect to the sewing ring.

In one embodiment, two handle members are attached to the housing and are oriented perpendicular to the housing axis. The shaft may be manually or automatically rotated around the housing axis. The blade comprises a cup having an open end and a closed end. The open end comprises a blade edge and is circular. The closed end comprises a cone shaped protrusion. The lower end of the shaft extends through the open end of the blade assembly and is attached to the closed end.

In one embodiment, a tool for coring a hole in a person's body is provided. The tool includes a housing with a first opening and a second opening and having an axis extending therebetween. A shaft is slidably and rotatably positioned along the axis. A blade assembly is attached to the shaft. The blade assembly comprises a cup having an open end and a closed end.

In one embodiment, the shaft extends through the open end and is attached to the closed end. The open end includes a blade edge. The blade edge is circular. The closed end is a cone. The shaft includes a first end protruding from the first opening and a second end protruding from the second opening. A ring is attached to the first shaft end and the blade assembly is attached to the second end. An interface is attached to the housing wherein the interface is shaped and dimensioned to communicate with a connector used to connect a medical device to a person's body.

In one embodiment, a method for coring a hole in a person's body is provided. A coring tool that includes a housing, a shaft moveably disposed within the housing, a blade assembly attached to the shaft, and an interface that is shaped and dimensioned to mate with a connector used to attach a medical device to person's body is provided. The connector is attached to the user's body. The interface is mated with the connector. The coring tool is actuated to core a hole in the person's body.

In one embodiment, the coring tool includes a blade assembly shaped like a cup having an upper open end and a conically shaped lower closed end. The upper open end of the blade assembly has a serrated cutting edge. The blade assembly is inserted into a preexisting opening in a patient's heart wall by extending and/or rotating the shaft such that the closed end of the blade assembly enters the person's body before the blade assembly. The shaft is retracted after the blade assembly enters the person's body. The shaft can be manually or automatically rotated during retraction. When the shaft is retracted, the open end of the blade assembly collects the severed portion of the heart wall, for example, and is pulled away from the person's body.

BRIEF DESCRIPTION OF THE DRAWINGS

For a further understanding of the present invention, reference may be had to the accompanying drawings, in which like numerals refer to like parts, elements, components, steps and processes, as follows:

FIG. 1 is a perspective view of a sewing ring attached to a portion of a heart with a crux cut shown in the spaced defined by the sewing ring.

FIG. 2A is a perspective view of a coring tool above a sewing ring attached to the human heart with a crux cut centered therein, with the blade of the coring tool shown retracted, prior to insertion of the cutting tool into the crux cut.

FIG. 2B is a perspective view of the coring tool of FIG. 2A with the blade shown extended after insertion of the blade assembly into the crux cut.

FIG. 2C is a perspective view of the coring tool of FIG. 2A as the blade assembly is forming a hole in the heart.

FIG. 3 is an exploded view to the coring tool of FIG. 2.

FIG. 4 is a sectional view of the coring tool of FIGS. 2A-2C taken along line 4-4 of FIG. 2B.

DETAILED DESCRIPTION

Figure 5:
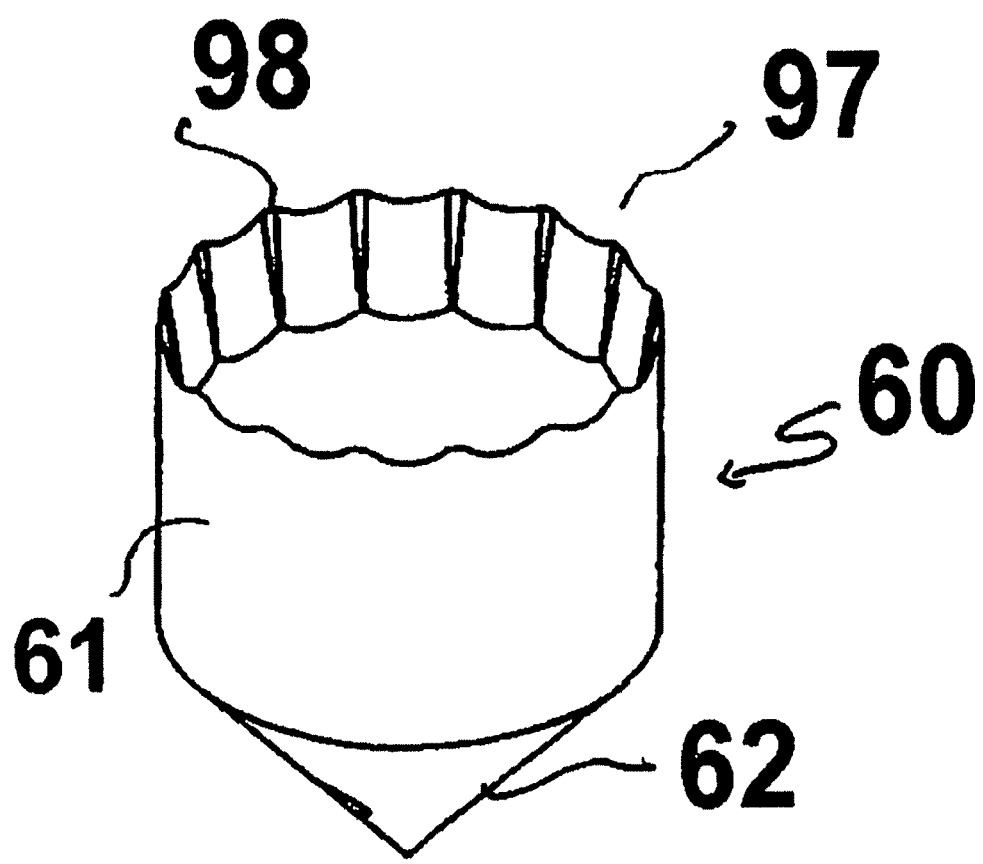
FIG. 5 is a perspective view of an alternate embodiment of the cutting blade assembly for the tool of the present invention.

Referring to FIG. 1, a portion of a ventricle wall 1 is shown with a connector 2 for a VAD attachment. In one example, the connector 2 is a sewing ring that is attached to the ventricle wall 1 through suturing. An exemplary connector can be found in the commonly owned United States patent application filed Dec. 8, 2005 for the invention entitled "Implant Connector" and naming Daniel Tamez, Vitrote Indravudh, Richard A. Marquis, Charles R. Shambaugh and Jeffrey A. LaRose as inventors, and having Ser. No. 11/298,410, the disclosure of which is hereby incorporated by reference.

In order to connect a VAD to the ventricle wall 1, a suitable hole must be formed in the space defined by sewing ring 2. Before using a coring tool, however, a surgeon must first form a "crux cut" 6 in the ventricle wall 1. The coring tool is then inserted into the crux cut 6 and actuated. The hole is then formed. The crux cut 6 is formed from a first incision 8 and a second incision 9. The first incision 8 and second incision 9 intersect to form a cross, hence the name "crux cut". In one example, a surgeon would form such a crux cut using a crux cutter. An exemplary crux cutter can be found in the commonly owned United States patent application filed on Jan. 13, 2006 naming Rajesh Pandey as inventor and entitled "Surgical Cutting Tool for Making Precise and Accurate Incisions, having Ser. No. 11/332,455, the disclosure of which is hereby incorporated by reference.

Referring to FIGS. 2A-2C, an exemplary embodiment of a coring tool 20 is shown for illustrative purposes. The coring tool 20 comprises a cylindrical housing sheath 30, a shaft 40, an actuating mechanism 50, a blade assembly 60, and handle members 70.

In one example, all of the components of the coring tool 20 are made of the same material (e.g. stainless steel). In another example, the cylindrical housing sheath 30, the shaft 40, the actuating mechanism 50, and the handle member 70 are made of one material, such as plastic, and the blade assembly 60 is made of another material, such as stainless steel. It will be understood that other combinations of materials are also possible depending on the needs of the end users and/or manufacturers.

Referring to FIG. 3, the cylindrical housing sheath 30 includes a first opening 31 and a second opening 32. The housing sheath defines a longitudinal axis A along which the operative elements of the coring tool 20 move back and forth. The lower end of the housing 30 is provided with an interface element 33 around the second opening 32. Interface element 33 in one example is a circular or annular ridge that extends out from the housing sheath 30 around the second opening 32. The annular ridge is adapted to engage the top annular surface of the sewing ring 2 when the coring tool is in use. In this way, the position of the coring tool in relation to the sewing ring is fixed when the tool is being operated.

Referring to FIGS. 3 and 4, in one example, the annular interface 33 has an outer diameter D of about 0.815 inches and a height H of 0.062 inches for use with a sewing ring having an outer diameter of 0.830 inches and a height of 0.090 inches. The Interface 33 is shown as being formed integrally with housing 30, but interface 33 could be a separate component that is affixed to housing 30 through other means or it could be retrofitted to an existing tool.

Shaft 40 is slidably and rotatably positioned within the cylindrical housing sheath 30 and is axially and rotatably moveable along axis A. The shaft 40 includes first end 41 and a second end 42. The shaft 40 is sufficiently long that first end 41 extends out of openings 31, 32 on housing 30 when blade assembly 40 is in an extended position (FIG. 2B). An exemplary length for shaft 40 is 3.70 inches given an exemplary length for housing 30 of 2.00 inches.

An actuating mechanism 50 is attached to first end 41 of shaft 40 and acts as a means to actuate coring tool 20 by pushing first end 41 toward the second opening 32 of housing 30, thereby extending blade assembly 60 from the housing sheath 30. Actuating mechanism 50 in one example is a thumb ring through which a surgeon can put a thumb. The thumb can also be used to draw shaft 40 away from the second opening 32 of the housing sheath 30 and thus move blade assembly 60 to the retracted position.

The blade assembly 60, in one example, comprises a cup shaped member having a cylindrical portion 61 and a cone shaped portion 62. Blade assembly 60 includes an open end 63 and a closed end 64. Open end 63 is located on one end of the cylindrical portion 61 and closed end 64 is located on one end of the cone portion 62. A blade edge 65 surrounds open end 63. Blade edge 65 in one example is circular. By applying blade edge 65 to tissue a hole can be cored in a person's heart. Advantageously, when a hole is cored in a person's heart, the cored tissue enters blade assembly 60 through open end 63. The tissue stays in blade assembly 60 until it can be retrieved by the surgeon. Cone portion 62 serves as a guide, which allows a user to pilot blade assembly 60 into a previously prepared crux cut before actuating coring tool 20 to create a hole. Blade assembly 60, in one example, is formed by machining a single piece. Exemplary dimensions for blade assembly 60 are 0.90 inches overall length, with a cutting diameter of 0.620 inches and a piloting angle of 38 degrees, and a depth for the tissue retrieval section of 0.460 inches.

Handle members 70 are connected to the housing sheath 30 and are arranged perpendicular thereto. Handle members allow a surgeon to grasp coring tool 20 to stabilize it and apply downward pressure if necessary. The surgeon can also rest his fingers either on the top sides 71 or bottom sides 72 of handle members 70 depending on the surgeon's needs during a procedure.

In one example, the blade assembly 60 is auto retractable through the provision of a resilient element, such as spring 80 disposed between housing 30 and shaft 40.

Referring to FIG. 4, shaft 40 is a cylinder having a first portion 81 and a second portion 82 in which the first portion 81 has a smaller diameter than the second portion 82. Exemplary diameters for the shaft 40 are 0.250 inches for the first portion 81 and 0.560 inches for the second portion 82. The difference in diameters forms a shoulder 83 on the shaft 40. The cylindrical housing sheath 30 includes a central bore 84 through which the shaft 40 extends and within which it moves back and forth in the axial direction. The bore 84 has a radially protruding annular ledge 85 through which the smaller diameter portion of the shaft 40 extends. The Spring 80 has a first end 87 that is positioned in engagement with the shoulder 83 of the shaft and a second end 88 that is positioned in engagement with the annular ledge 85 formed within the central bore 84 of the housing 30. Accordingly, shaft 40 and blade assembly 60 are biased by spring 80 in the retracted position.

Referring further to FIGS. 3 and 4, the various components of the coring tool 20 are interconnected by threaded engagement. For instance, shaft 40 has a threaded opening 91 by which a threaded protrusion 92 on the actuating mechanism or ring 50 threadedly engages the shaft 40. Similarly, arm members 70 have threaded protrusions 93 that engage threaded openings 94 on the sidewall of the housing sheath 30. Finally, the closed end 64 of blade assembly 60 has a threaded opening 95 in which a threaded protrusion 96 from shaft 40 is engaged. It should be noted that this means of attaching the components of core cutter 20 is provided for illustrative purposes only. Other means are also available depending on the materials used to form core cutter. For example, press-fitting the components together, laser welding, or gluing. The body and handles could also be formed in a single piece with injection molding, as could the shaft and ring, if those components were made of plastic or a metal capable of being injection molded.

Referring to FIGS. 2A-2C, to core a hole in a person's heart, a surgeon or other user, attaches a connecting device, such as a sewing ring 2 to a patient's ventricle 1.

The surgeon will make the crux cuts 8 and 9. Then, the surgeon pilots the coring tool 20 into the space 4 defined within the circumference of the sewing ring 2 by communicating the interface 33 with sewing ring 2. The surgeon, if necessary, applies downward pressure on the ridge handle members 70 or simply rests his fingers on the handle members. If necessary, the surgeon inserts a thumb into ring 50. The surgeon actuates the cutting tool 20 by pressing the end 41 of the shaft 40 in the direction of the arrow shown in FIG. 2B. The blade assembly 60 enters into the ventricle until the entirety of the blade assembly 60 is in the ventricle 1. The surgeon then either (1) removes pressure from the shaft 40 and thereby allows the spring 80 to push the shaft and blade assembly up and out of the user's body or (2) applies upward pressure through utilization of ring 50 to propel blade assembly out of the heart in the direction of the arrow shown in FIG. 2C. In either case, the blade edge 65 (FIG. 3) engages the ventricle wall 1 from within the ventricle and makes a hole as it cuts through the heart wall. If need be, the surgeon can also rotate the shaft 40 around axis A to provide a rotational cutting force by the blade edge 65. The cored tissue enters opening 63 of blade assembly 60 (FIG. 3) and remains therein. The surgeon can then retrieve the cored tissue after disengaging the coring tool 20 from the sewing ring 2.

The hole formed in the ventricle wall 1 must be of a suitable size and shape to receive an inflow tube from the VAD. An exemplary hole would be one of generally circular shape and having a diameter of 15.7 mm, although the size and the shape of the hole will vary depending on the size and shape of the inflow tube on the VAD. Accordingly, for 15.7 mm diameter hole, the blade edge 65 surrounding open end 63 of blade assembly should be circular and have a diameter of 15.7 mm.

Referring to FIG. 5, there is shown an alternative embodiment for the cutting blade assembly of the present invention. The blade assembly 60 consists of the cylindrical portion or container 61 having an open upper end and a closed lower end consisting of a conical portion 62. It will be understood that the closed lower end of the container 61 need not be conically shaped. In this embodiment the margin of the upper open end of the container 61 is formed with serrations 97 defining a plurality of marginal tooth-like projections 98 extending upwardly and outwardly in a direction slightly away from the longitudinal axis of the blade assembly. The tooth-like projections are spaced apart by concave portions of the sidewall of the container. In this embodiment the entire circumference of the edge of the open end of the blade assembly is serrated, although the present invention does not require this arrangement. Such serrations facilitate cutting of the heart wall from the inside as the blade assembly is withdrawn from the heart. It will be understood by those skilled in the relevant art that various forms of serrations, including without limitation tooth-like projections separated by convex or other shaped portions of the sidewall of the container, can be employed on the blade assembly as desired without departing from the scope of the present invention.

Figure 6:
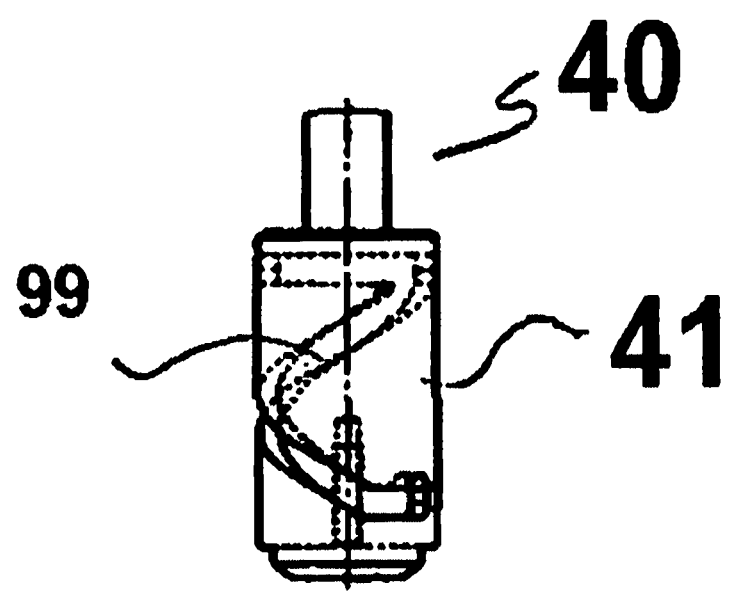
FIG. 6 is a side elevation of a portion of an alternate embodiment of the central shaft for the tool of the present invention.

Referring to FIG. 6, there is depicted an alternate embodiment of the upper portion of the coring shaft 40 In this embodiment the shaft and the attached blade assembly may be automatically rotated as the shaft is moved back and forth axially within the surrounding housing sheath 30. In this embodiment, the enlarged first end 41 of the shaft 40 may be provided with a helical slot or groove 99 which extends substantially from the top to the bottom of the enlarged end of the shaft as it winds around the circumference thereof. An appropriate pin or set screw (not shown) carried by the housing sheath 30 is adapted to engage and ride in the slot or groove 99. As pressure is applied to the shaft through the actuating ring 50 to move it axially within the housing sheath, the engagement between the slot and the pin as the shaft moves will cause the shaft with the blade assembly attached at its lower end to rotate. It is therefore unnecessary to apply both longitudinal and rotating pressure on the shaft when using the tool. It will be understood that the helical slot or groove could be formed in the interior surface of the bore formed through the housing sheath and the engaging pin provided as part of the movable shaft without departing from the scope of the present invention. To the extent that the coring tool retains the ring 50 for actuating the tool, the ring may be rotatably mounted at the top of the shaft so that it does not have to rotate with the shaft as the latter is moved within the housing sheath.

Figure 7:
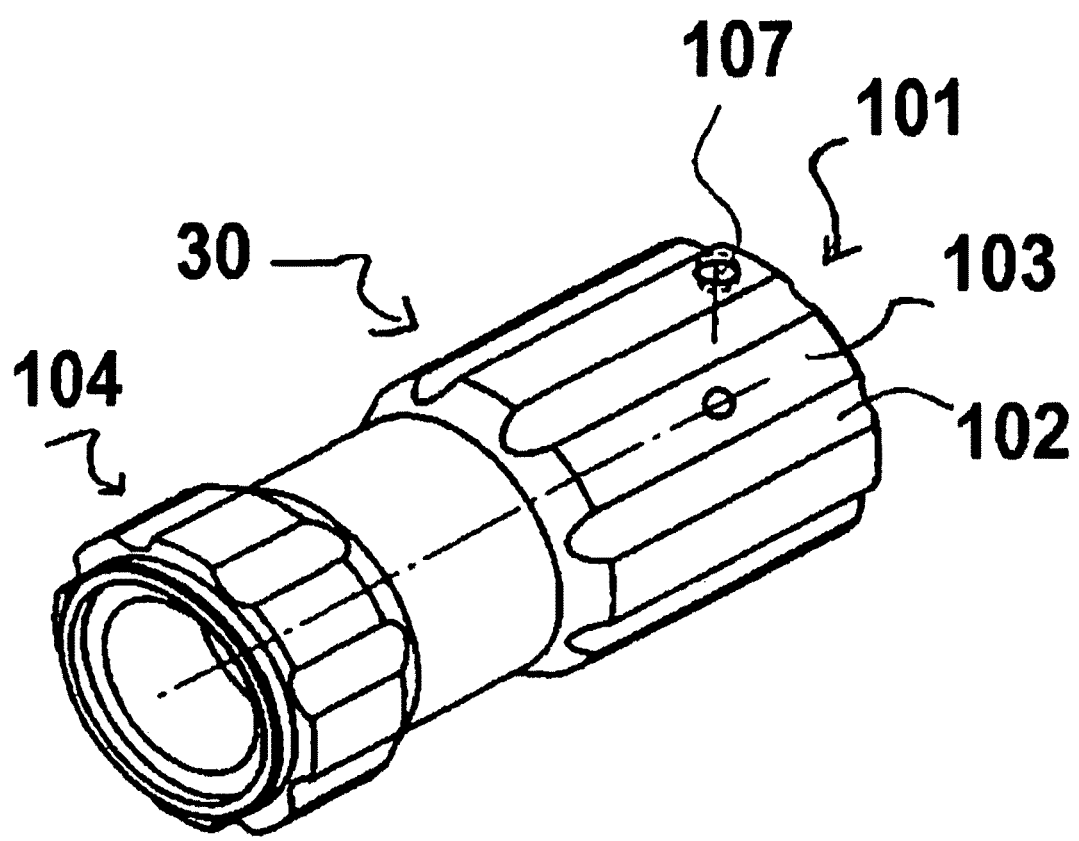
FIG. 7 is a perspective view of an alternate embodiment of a handle for the tool of the present invention.
Figure 8:
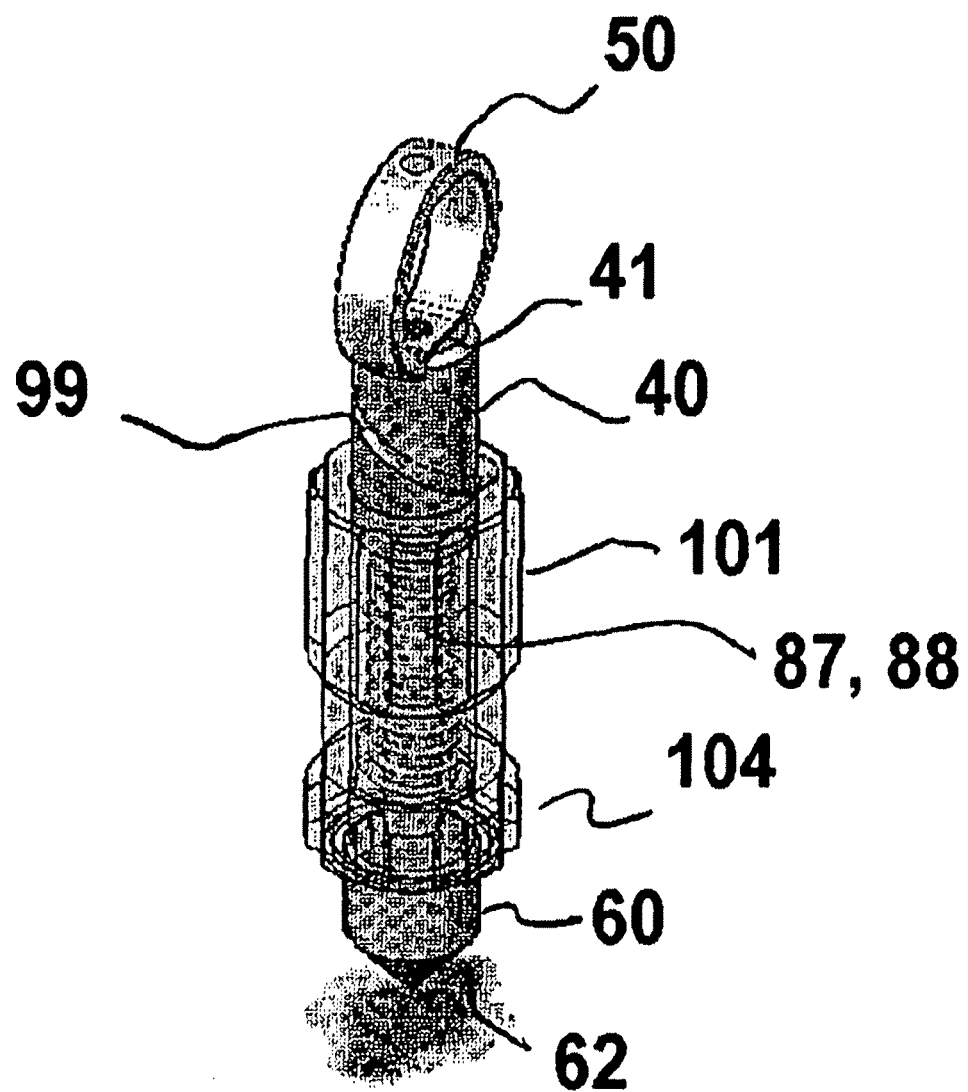
FIG. 8 is a perspective view of an alternate embodiment of the tool of the present invention.

Referring to FIGS. 7 and 8, there is depicted an alternative embodiment for the housing sheath 30. In this embodiment, the outer surface of the housing sheath is provided with at least one knurled portion 101 defined by a plurality of longitudinally or axially extending ridges 102 spaced apart by raised sections 103 to facilitate gripping. The ridges 102 may be provided around the entire circumference of the housing sheath. As shown, there may be a second knurled portion 104 formed on the housing sheath and spaced from the first knurled portion 101 by a circumferential recess 106. In this embodiment the pair of handles 70 may be eliminated.

When the upper portion 41 of the shaft 40 is helically slotted as described above, the knurled or ridged housing sheath 30 may have a threaded recess 107 to engage a set screw that would extend radially inwardly to engage the helical slot. It will be understood that the nature and direction of the ridges and the location of the helical slot and engaging pin or set screw can be altered without departing from the scope of the present invention. In such an embodiment, once the annular interface 33 is engaged with the sewing ring and the tool is thereby properly oriented, the tool may be actuated either by holding the knurled housing sheath 30 and moving the shaft by applying axial pressure to the shaft through the ring 50, or by applying axial pressure to the housing sheath to move up or down relative to the shaft, as desired. In either case, the engagement of the pin in the helical slot will cause the shaft to move in the desired axial direction. Assistance in withdrawing the tool from the heart may still be provided as a result of the bias induced by the spring 87, 88.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A surgical tool assembly comprising:
a sheath having an open distalmost end defining a blade assembly exit region;
a connector defining a surface area configured to be disposed adjacent a target tissue wall of a patient when the connector is attached to the target tissue wall;
a peripheral ridge extending from and surrounding the entire open distalmost end of the sheath, said peripheral ridge having a surface adapted to mate with a corresponding surface of the connector to center the open end of said sheath over said surface area, wherein the connector is configured to releasably receive and orient the peripheral ridge in a predetermined fixed position adjacent said surface area after said connector is attached to said target tissue wall; and
a blade assembly removably mounted on a shaft and arranged for movement between a retracted position within the open end of said sheath and an extended position away and exposed from the sheath and from the peripheral ridge, the shaft having a helical slot and the sheath having a pin follower slideable within said helical slot and defining a rotation path of the blade assembly, whereby axial movement of said shaft causes said blade assembly to rotate, said blade assembly being a cup defining an opening and comprising a peripheral cutting edge of a predetermined shape facing away from said surface area when the blade assembly is in said retracted position and facing toward said surface area when the blade assembly is in said extended position, said cutting edge configured to sever a portion of the target tissue wall within said surface area upon withdrawal of the blade assembly from said extended position to said retracted position, thereby to form a hole having said predetermined shape in the target tissue wall.

2. The surgical tool assembly of claim 1 in which said target tissue wall comprises the muscular tissue of a heart.

3. The surgical tool assembly of claim 1, in which said shaft is slidable for movement back and forth within said sheath, said shaft having an actuating mechanism comprising a ring attached to the shaft through which a user can insert a thumb or finger to apply pressure to move the shaft.

4. The surgical tool assembly of claim 3, wherein the shaft is rotatable around the longitudinal axis of said sheath such that a user can apply rotational force to said blade assembly when cutting a hole in said target tissue wall.

5. The surgical tool assembly of claim 1, in which the predetermined shape of said peripheral cutting edge is substantially annular whereby the hole formed in the target tissue wall is substantially circular.

6. The surgical tool assembly of claim 1 further comprising a perimeter of the opening to said cup defining said peripheral cutting edge, said cup configured to retain the severed portion of the tissue wall in said retracted position.

7. The surgical tool assembly of claim 6, wherein the cup comprises a cone shaped protrusion that is used to pilot the cup through a preexisting cut in the target tissue wall.

8. The surgical tool assembly of claim 1 in which said connector comprises a sewing ring.

9. The surgical tool assembly of claim 8 in which said sewing ring is configured to be connected to the myocardium of a heart.

10. The surgical tool assembly of claim 8, further comprising two handle members attached to and protruding in opposite directions from the sheath to allow a user thereof to apply pressure on the sheath to maintain the open end of the sheath in engagement with said sewing ring when operating the surgical tool assembly.

11. The surgical tool assembly of claim 8, wherein said peripheral cutting edge is centered with respect to the open end of said sheath during movement of said blade assembly between said retracted and extended positions such that a hole formed in the target tissue wall is centered with respect to the sewing ring.

12. The surgical tool assembly of claim 8 in which the mating surfaces of said ridge and sewing ring are annular.

13. The surgical tool assembly of claim 1 in which said peripheral cutting edge comprises a plurality of side-by-side scalloped segments defining tooth-like projections therebetween.

14. The surgical tool assembly of claim 13 in which said scalloped segments collectively define a circumferential cutting perimeter of said peripheral cutting edge.

15. The surgical tool assembly of claim 14 in which each of said scalloped segments is obliquely angled outwardly relative to a longitudinal axis of said blade assembly collectively to define a splayed circumferential cutting perimeter.

16. The surgical tool assembly of claim 13 in which each of said scalloped segments comprises a concave cutting edge collectively defining said tooth-like projections.

17. The surgical tool assembly of claim 1 in which said peripheral cutting edge is serrated.

18. The surgical tool assembly of claim 1, further comprising a biasing element which biases the blade assembly toward the open end of the sheath.

19. The surgical tool of claim 1, wherein the peripheral ridge extends out from the sheath around the open end.

20. The surgical tool of claim 1, wherein the peripheral ridge has an outer diameter of 0.815 inches and a height of 0.062 inches.

21. The surgical tool of claim 1, wherein the peripheral ridge is formed integrally with the sheath.

22. The surgical tool of claim 1, wherein the peripheral ridge is separate from and affixed to the sheath.

* * * * *